United States Patent [19]

Sauter et al.

[11] Patent Number: 5,461,229
[45] Date of Patent: Oct. 24, 1995

[54] ON-THE-GO OPTICAL SPECTROSCOPY SOIL ANALYZER

[75] Inventors: Gerald F. Sauter, Eagan; George F. Nelson, Coon Rapids, both of Minn.

[73] Assignee: Unisys Corporation, Blue Bell, Pa.

[21] Appl. No.: 254,903

[22] Filed: Jun. 6, 1994

[51] Int. Cl.$^6$ .................................................. G01N 21/35
[52] U.S. Cl. .................. 250/253; 250/339.12; 250/341.2
[58] Field of Search .............................. 250/253, 339.07, 250/339.08, 339.14, 341.1, 341.6, 358.1, 359.1, 340, 339.11, 339.12, 341.2, 341.8

[56] References Cited

U.S. PATENT DOCUMENTS

| | | | |
|---|---|---|---|
| 3,428,806 | 2/1969 | Wack | 250/253 |
| 4,247,770 | 1/1981 | Welch | 250/253 |
| 5,065,019 | 11/1991 | Darilek et al. | 250/253 X |
| 5,070,242 | 12/1991 | McCelland et al. | |
| 5,075,552 | 12/1991 | McCelland et al. | |
| 5,241,179 | 8/1993 | Carrieri | 250/341.6 |

Primary Examiner—Carolyn E. Fields
Assistant Examiner—Edward J. Glick
Attorney, Agent, or Firm—Glenn W. Bowen

[57] ABSTRACT

An on-the-go probe for determining the presence of chemical residue in a soil using Transient Infrared Spectroscopy by pulling a soil implement through the soil with the soil implement having a heating or cooling source for temporarily creating a temperature differential between a layer of soil proximate the soil implement and a layer of soil remote from the soil implement, and moving the soil sufficiently fast with respect to heating source to enable measuring the radiation characteristics of the thin layer of soil before the thin layer of soil begins to self-absorb and substantially change its emission characteristics.

13 Claims, 2 Drawing Sheets

ON-THE-GO OPTICAL SPECTROSCOPY SOIL ANALYZER

FIELD OF THE INVENTION

This invention relates to field measurements of soil chemicals and, more specifically, to on-the-go measurements of the amount and type of soil chemicals in the soil and the use of the on-the-go measurements for on-the-go control of the amount of chemicals to apply to the soil.

BACKGROUND OF THE INVENTION

Agricultural use of chemicals requires periodic soil analysis. Generally, chemical soil analysis for use in herbicide and fertilizer applications requires that soil samples be taken from various portions of the field and then submitted to a laboratory. One of the difficulties with the process is that it usually takes weeks to obtain the results of the soil test from the laboratory. Another of the difficulties is sampling error; that is, the concentrations of chemicals can vary from one portion of the field to another portion of the same field. At best, one obtains an average of the chemicals in the soil.

In addition for the need to determine the chemical residues from farming, one may need to determine the chemical residues from industrial processes such as military operations (i.e., chemical residues such as explosives, propellants, fuels, lubricants) and industrial manufacturing (i.e., chemical residues such as Volatile Organic Compounds (VOCs), and Dense Non-aqueous Phase Liquids (DNAPLs))

One of the problems with detection of the chemical residues in soils is that many chemical residues do not exhibit substantial fluorescence, thus hindering detection of their presence in subsurface soil. In general, a probe is inserted into the soil, and a light source located in the probe directs light through a window in the probe and into the soil where a portion of the light is absorbed by chemicals in the soil These chemicals fluoresce resulting in an optical emission different from the incident light.

One of the methods of determining chemical residues in soil is with a spectroscope. One spectroscopic method uses a scanning spectroscope which uses a narrow bandwidth filter which scans soil sample emissions throughout the emission spectrum while producing an electrical output from a single detector. A disadvantage of this system is the possibility that, during the scan, some spectral lines will not be present throughout the scan resulting in uncertain soil residue measurements of the soil sample emission spectra.

Another method is the use of a Fourier Transform Infrared spectroscope which simultaneously views the entire emission spectrum of the soil sample and then converts the measured output to a soil sample emission spectra which reveals the chemical residues in the soil.

Through the use of transient infrared spectroscopy (TIS), many of the chemical residues can be identified, the concentration levels measured, and a three-dimensional site characterization of the soil contaminants can be logged and plotted in real time. Thus, the TIS provides an in situ measurement of chemical residue in the subsoil.

The present invention provides a method and apparatus for use in agricultural and environmental remediation applications to enable TIS to determine both the concentration of farm chemicals in the soil and their spatial distribution. This knowledge allows application of precise quantities of corrective farm chemicals such as fertilizers and herbicides to areas of the field needing them and determination of the concentrations of contaminating chemicals from commercial activities.

In general, TIS is used to detect the chemicals present in a moving solid stream by measuring changes in emissions in the mid-infrared spectrum (400 to 4000 $cm^{-1}$ wave number or 25 to 2.5 micron wavelength) of the moving solid. This portion of the spectrum is well suited for soil analysis since it can provide information on the kinds and quantifies of chemical residue occurring as a result of agricultural applications of fertilizers, pesticides and herbicides One of the problems with TIS is the high absorption rams in the mid-infrared spectrum of most solids. If the sample being analyzed is thick, the high self-absorption rates produce an emission spectrum resembling a featureless, blackbody. To avoid the self-absorption problem occurring with thick samples, only a very thin sample is analyzed. In Transient Infrared Spectrometry, one measures the emission characteristics of a thin sample. TIS avoids the self-absorption problem by measuring thermal emission behavior of a thin sample of a larger body before the thin sample comes into thermal equilibrium with the larger body and begins to self-absorb like a blackbody.

During the conventional TIS process, the solid moves through the field of view of an infrared spectroscope and, as it does so, the solid is subjected to thermal energy by a jet of either hot or cold gas, a heated platen, a laser beam, or a UV or incandescent lamp. The thermal energy strikes the surface of the solid producing a thin hot or cold layer at the surface of the solid. As the thermal energy begins to dissipate, the thin layer of excited solid begins to thicken rapidly, but before the thermal emissions of the thickened layer can be measured, the solid is moved from the field of view of the infrared spectroscope and a thin, newly excited solid is moved into the field of view. As a result, the layer within the field of view of the spectroscope is constantly replenished and remains thin and thus not subject to thick sample errors.

If the solid sample is heated, a thin layer on the solid sample becomes an emission source independent of the bulk of the solid. As long as the excited layer on the solid remains thin, the emission self-absorption is at a minimum and the observed spectrum is of a thin sample.

If the solid sample is cooled, the thin layer acts as a thin transmission sample, and the bulk of the material beneath the thin layer radiates its blackbody spectrum through the cold layer. The spectroscope observes the featureless, blackbody spectrum of the solid sample with the structured transmission spectrum of the cold layer superimposed on the blackbody spectrum of the cold layer. Signal processing removes the blackbody spectrum, thus leaving the spectrum of the molecular constituents in the thin surface layer.

In the present invention, the necessary movement of the soil past the probe is obtained by either a forward motion of the probe through the soil or use of a rotating heat source within the probe.

The present process and apparatus permits a user not only to measure the chemical content and fertilizer deficiencies of the soil on-the-go, but also allows the person to use the on-the-go measurements to control of the mount of chemical metered onto the soil.

BRIEF DESCRIPTION OF THE PRIOR ART

U.S. Pat. No. 5,075,552 describes the method for transient thermal infrared emission spectrometry. In the method, heat is applied to the surface of an object to cause thermal emission of infrared radiation from the thin surface layer portion. If one waits to measure the thermal emission, the thin layer begins to self-absorb radiation from the subsurface layers. By moving the material through a spectroscope before the temperature can equalize throughout the material, one is able to measure and analyze the thermal emission from the thin surface layer portion U.S. Pat. No. 5,070,242 describes the method for transient thermal infrared emission spectrometry where the thin surface layer portion is cooled and the measurements of the infrared emission are made before the thin surface layer portion begins to self-absorb the radiation.

SUMMARY OF THE INVENTION

Briefly, the invention comprises an on-the-go probe for determining the presence of materials in soil using TIS by pulling a soil implement having a probe through the soil, or by pushing the sensor into the soil for environmental contamination characterization, with the soil implement having a heating or cooling source for temporarily creating a temperature differential between a thin layer of soil proximate the soil implement and the subsoil adjacent to the thin layer of soil. In the preferred embodiment, one moves the soil implement sufficiently fast with respect to the thin layer of soil to enable measurement of the radiation characteristics of the thin layer of soil before the thin layer of soil begins to self-absorb and substantially change its emission characteristics.

DESCRIPTION OF THE PREFERRED EMBODIMENT

Figure 1:
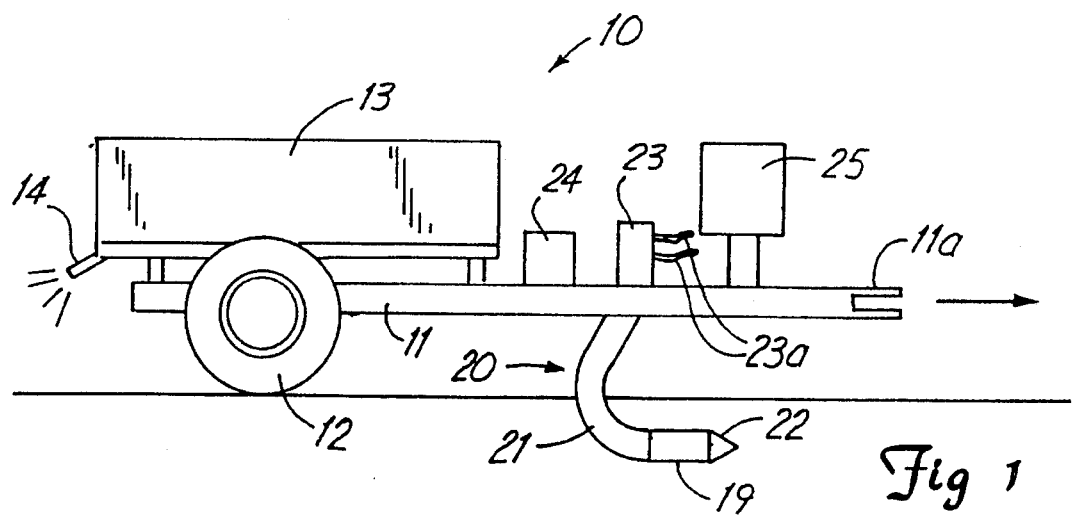
FIG. 1 shows a fertilizer applicator having a soil probe for on-the-go measurement of the chemicals in the soil and on-the-go control of the fertilizer applied to the soil.

FIG. 1 reference numeral 10 generally identifies an on-the-go system for measuring soil chemicals and applying corrective chemicals. A soil implement 20 is attached to a frame 11 which has one end supported by a pair of wheels 12 and the other end supported and pulled by a tractor or truck (not shown) which attaches to a hitch 11a. In the embodiment shown, a fertilizer tank 13 is carried on frame 11 with spray nozzles 14 connected to the fertilizer tank to permit spraying of fertilizer on the field. A set of nozzle controls 24 permit measured application of fertilizer to the filed.

Soil implement 20 is shown moveably attached to frame 11 by a two-way hydraulic mechanism 23 which permits raising or lowering the soil implement; that is, the soil implement has a shank 21 with a probe 19 having a cone point 22 which moves through the soil as the system 10 is pulled by a tractor or the like. The hydraulic connections 23a allow one to place the soil-sensing probe 19 to the proper depth for soil analysis or in a reduced friction and wear implementation it could be a plate or shoe which is dragged over the surface of the soil after a plow and performs the same measurements as above.

Figure 2:
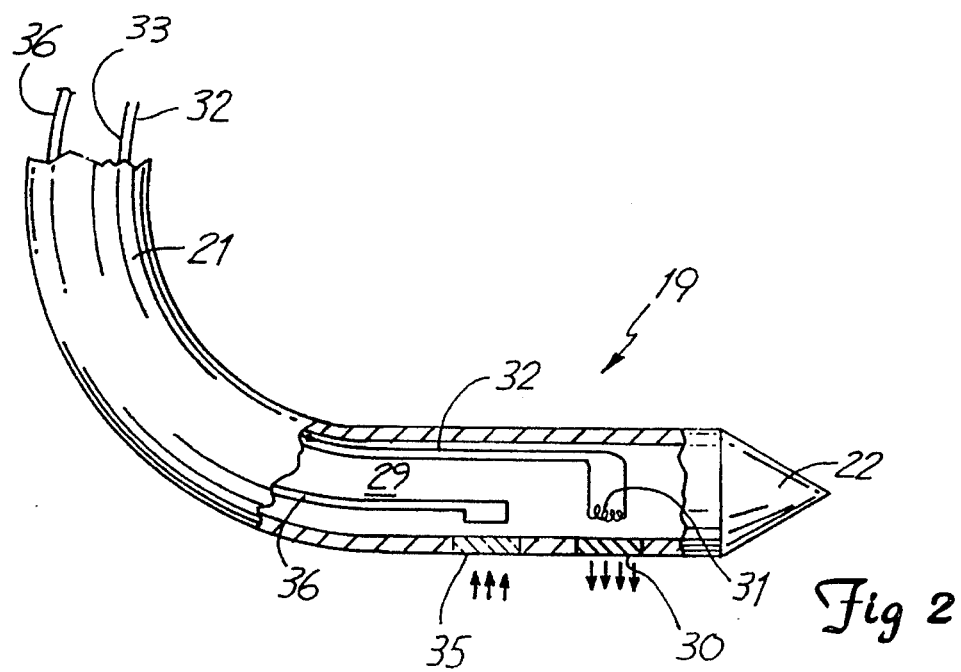
FIG. 2 shows a partial cutaway view of the probe of FIG. 1.

FIG. 2 shows a partial cutaway view of probe 19 of the present invention. The soil implement 21 includes a conical drive point 22 for parting the soil and a shank 21 having a probe 19 having a chamber 29 holding a heating ribbon 31. Ribbon 31 heats a metal heat-conducting element 30 which contacts soil 9 adjacent probe 10. The arrows indicate the heating of a thin layer of the soil. Located rearward of heating dement 30 is an optical window 35 which permits passage of infrared thermal radiation from a thin layer of heated soil through window 35 and into an optic cable 36 where they are transmitted to the TIS unit where the signals are compared to known material to determine the chemical content of the soft. In an alternate embodiment one could place the analyzer in the probe.

Figure 3:
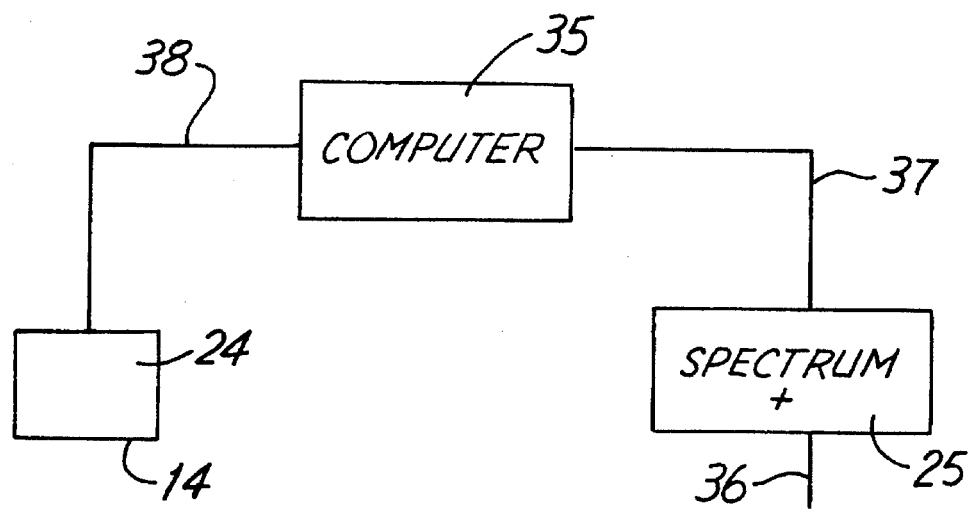
FIG. 3 shows a schematic of the control system for measuring soil chemicals and comparing the soil chemicals with a reference base to obtain a control signal to control the amount of fertilizer spread on the field.

FIG. 3 shows a schematic of the control system using TIS methods. The measured infrared radiation is sent by optical cable 36 to spectrum analysis unit 25 where it is analyzed. Next the signal is sent over cable 37 to a computer 35 which retains information on the proper levels of chemicals in the soil. After computer 35 completes comparisons of the output from the spectral analysis unit 25 with the reference base in the computer 35, the computer generates a corrective signal that is sent via cable 38 to valve controller 24. Valve controller 24 opens and closes valves to apply corrective chemicals in accordance with preprogramed soil needs. For example, if the chemical analysis indicates a nitrogen deficiency for the particular crop being raised on the soil, valve controller 24 opens the valves to apply nitrogen to the soil in accordance with the signal generated by computer 35.

FIG. 1 shows how one can measure agriculturally related chemicals in soils with the motion of the sample a result of the forward motion of the farm implement. The heating or cooling can be introduced directly to the soil and, at the desired depth, by attaching the heating or cooling source and spectroscope to a plow or some implement that is dragged behind a tractor. The advantage of this method is its simplicity since the soil measurement can be made in situ Another alternate method involves lifting a soil sample from the desired depth and transporting the soil sample to a hot or cold source and an above-ground detector on the tractor. The advantage of this method is it allows the soil sample to pass the thermal source at a speed independent of the speed of the implement being pulled through the soil Heating of the soil sample requires raising the temperature of a very thin layer of the soil sample, typically a thickness of 20 to 30 micro inches, to a higher temperature than the surrounding soil. The measurement temperature of the sample can range from 4° C. above ambient, to the order of 150° C. above ambient. The optimum temperature to produce a measurement can readily be determined for various soil matrices and soil moisture content.

Measurements may be taken by moving the probe either horizontally or vertically through the soil. In addition, the path of the thermal heating of the soil can be linear (up and down with the probe) or it may be helical. Rotational motion of the thermal source and sensing device, together with either linear motion through the soil, produces a helical path for the probe. Many more measurements of the soil can be made with the helical path method. which produces a much more representative average condition of the soil matrix.

Figure 4:
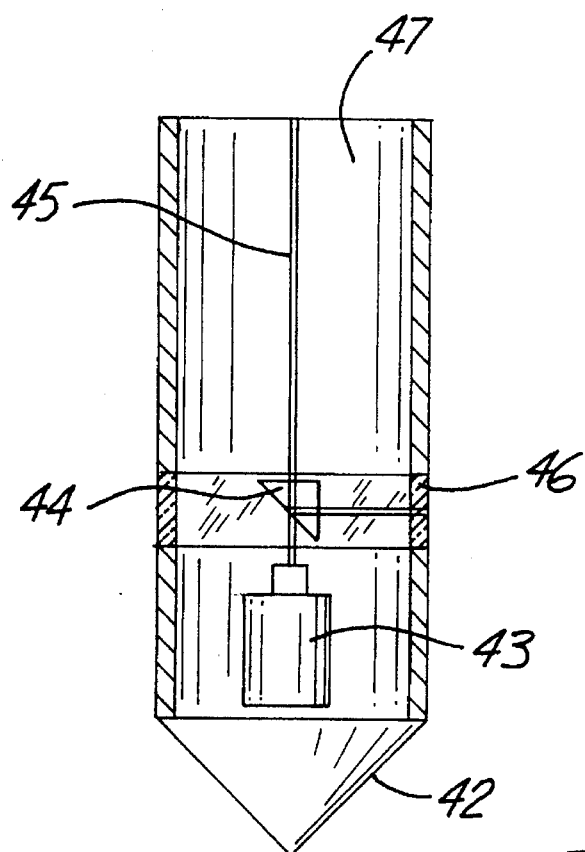
FIG. 4 shows an alternate embodiment of a probe for measuring the emission of a soil sample located around the outside of the probe.

FIG. 4 shows a probe 40 for inserting vertically and taking measurements as the probe is forced into the soil. Probe 40 includes a cone tip 42 for penetrating the soil with probe 40 having a chamber 47 and a 360-degree optical window 46.

Located in chamber 47 is a motor 43 for rotating a mirror or prism for transmitting an infrared signal out window 46 and into the surrounding soil 9. The reflected signal passes through mirror or prism 44 and up a separate optical cable to the soil analysis unit located above ground. In this embodiment, one can pulse the infrared radiation through cable 45 to obtain the desired thin soil sample radiation spectrum.

While FIG. 2 shows a wire heating dement, a variety of thermal sources can be used to heat the soil including (1) heated platens, (2) heated ribbons, (3) UV/IR lasers, (4) broad spectrum sources such as UV flash lamp and incandescent sources, and (5) natural friction present from pushing the probe through the soil.

Of the heat sources described, a heated platen thermal source is the least complex and most durable thermal sources It can be incorporated into the outer wall of the probe and fabricated from high abrasion-resistant materials, which are commonly available. Because of its simplicity and low cost a heated platen is preferred in many applications.

Another thermal source is a laser thermal heat source. The laser thermal source offers distinct advantages because the thermal energy can be directed onto the soil matrix surface without heating the intervening materials or the soil probe. In addition. the laser thermal heat source can be pulsed to repeatedly produce a thin thermally excited layer for measurement even though the probe is not being forced through the soil. In addition, pulsing the lasers permits small lasers to produce very 1-dgh-peak optical power for their sizes. Another advantage of the use of lasers for a thermal source is that the laser can be remotely placed from the cone penetrometer probe and coupled to the probe via optical fiber.

Another method of heating a thin layer of soil proximate the probe is friction. If the friction encountered in forcing the probe through the soil is transferred to the soil around the probe, the necessity for a separate heat source can be eliminated.

Thus, with the present invention, in situ measurements of the chemical residues can be made in real time and on-the-go. The information can be used for on-the-go application of corrective chemicals such as herbicides, pesticides, or fertilizers. In other applications such as measuring industrial chemical residue or military chemical residue, one may criss-cross the affected area to generate a grid of the field with the concentrations of chemical residues at various positions on the field. In this application corrective chemicals would not be applied but portions of the soil in the field with unacceptable chemical residues would be removed and taken to an area where the contaminated soil can be stored or the chemical residue removed.

We claim:

1. An on-the-go probe for determining the presence of materials in a soil comprising:

a soil implement for pulling through the soil, said soil implement having a chamber therein;

means on said soil implement for creating a temperature differential between a layer of soil proximate said soil implement and a layer of soil remote from the soil implement by raising the temperature sufficiently high to generate a measurable thermal radiation change in a thin layer of soil proximate the soil implement;

a window located in said soil implement for transmission of the measurable thermal radiation change to a receiving instrument in the soil implement; and further means for moving the soil implement sufficiently fast with respect to the thin layer of soil to enable measuring the radiation characteristics of the thin layer of soil before the thin layer of soil thickens sufficiently to substantially change its emission characteristics.

2. The on-the-go probe of claim 1 wherein said on-the-go probe includes an apparatus Ibr directing chemicals on to the soil in response to a measurement of materials in the soil.

3. The on-the-go probe of claim 1 wherein said on-the-go probe includes a heating element for heating the soil proximate the soil implement.

4. The on-the-go probe of claim 3 wherein the heating element comprises a ribbon heating element.

5. The on-the-go probe of claim 1 including a hydraulic cylinder for controlling the depth of the soil implement in the soil.

6. The on-the-go probe of claim 1 including a tank for holding a herbicide and means for spraying the herbicide on the ground in response to a measurement of contaminants in the soil.

7. The on-the-go probe of claim 1 including a tank for holding fertilizer and means liar spraying the fertilizer on the ground in response to a measurement of fertilizer deficiencies in the soil.

8. The on-the-go probe of claim 2 including a computer for comparing a measured signal from the on-the-go probe to a reference in the computer to determine a correctable amount of chemical to be applied to the soil in accordance with the measurements.

9. The on-the-go probe of claim 8 wherein the computer controls valves for increasing and decreasing the amount of chemical to be applied to the soil in accordance with a signal generated by the computer.

10. The on-the-go probe of claim 9 wherein the probe is directed vertically into the ground and the means on said soil implement pulses infrared radiation into the soil.

11. A method of producing in real time a sensor-proximate analysis of soil through optical spectroscopy comprising the steps of:

pulling an on-the-go probe through the soil;

irradiating the soil proximate the on-the-go probe to measurable radiation changes in a thin layer of soil proximate the on-the-go probe;

measuring the measurable radiation changes in a thin layer of soil proximate the on-the-go probe before the thin layer of soil thickens sufficiently to substantially change its emission characteristics; and analyzing the thin layer of soil with a spectrometer to determine correctable deficiencies in the soil;

generating a control signal in accordance with the correctable deficiencies in the soil; and applying a corrective chemical to the soil in accordance with a preprogramed schedule of responses for measured deficiencies.

12. An on-the-go probe for determining the presence of chemical residues in a soil comprising:

a soil implement located proximate a surface of the soil for displacement relative to the soil, said soil implement having a chamber therein;

a radiation source on said soil implement for creating a measurable temperature differential between a surface layer of soil proximate said soil implement and a layer of soil remote from the soil implement to generate a temporary and reversible measurable thermal radiation change in a thin layer of soil proximate the soil implement;

a window located in said soil implement for transmission of an emission spectra from the thin layer of soil proximate the probe to a receiving instrument in the soil implement; and a member for moving the soil implement sufficiently fast with respect to the thin layer of soil to enable measuring the radiation characteristics of the thin layer of soil before the thin layer of soil thickens sufficiently to substantially change its emission characteristics.

13. An on-the-go probe for determining the presence of chemical residues in a soil comprising:

a soil implement for displacement relative to the soil, said soil implement having a chamber therein;

a radiation source on said soil implement for creating a measurable temperature differential between a layer of soil proximate said soil implement and a layer of soil remote from the soil implement to generate a measurable thermal radiation change in a thin layer of soil proximate the soil implement;

a window located in said soil implement for transmission of an emission spectra from the thin layer of soil proximate the probe to a receiving instrument in the soil implement; and a member for moving the soil implement sufficiently fast with respect to the thin layer of soil to enable measuring the radiation characteristics of the thin layer of soil before the thin layer of soil thickens sufficiently to substantially change its emission characteristics; and a spectrometer for measuring the radiation characteristics for determining the chemical residue in the soil and a computer for comparing the measured signal to a reference signal and means for applying corrective chemicals to the soil in accordance with the determined chemical residue measurements.

* * * * *